United States Patent
Budmiger

[11] 3,943,573
[45] Mar. 16, 1976

[54] AUTOMATIC PROTECTIVE SHADE EQUIPMENT ON PROTECTIVE VISORS, PROTECTIVE HELMETS OR PROTECTIVE GOGGLES, PARTICULARLY FOR FUSION WELDING

[75] Inventor: Hermann Budmiger, Seewen, Switzerland

[73] Assignee: UTP Arbeitsschutz AG, Rheinfelden, Switzerland

[22] Filed: Mar. 19, 1974

[21] Appl. No.: 452,580

[30] Foreign Application Priority Data
Mar. 26, 1973  Switzerland............................ 4377/73
Sept. 17, 1973  Switzerland........................ 13313/73

[52] U.S. Cl............................. 2/8; 2/14 K; 351/45; 351/49
[51] Int. Cl.² ............................. G02C 7/16; G02C 7/12
[58] Field of Search ............ 351/44, 47, 45, 48, 49, 351/57, 58; 2/8, 14 J, 14 XS, 14 K

[56] References Cited
UNITED STATES PATENTS

| | | | |
|---|---|---|---|
| 2,548,230 | 4/1951 | Molyneux | 2/8 X |
| 3,095,575 | 7/1963 | Radar | 351/44 X |
| 3,096,430 | 7/1963 | Farr | 2/8 X |
| 3,159,844 | 12/1964 | Habouch | 2/8 |
| 3,238,535 | 3/1966 | Richey | 2/8 |
| 3,245,315 | 4/1966 | Marks et al. | 351/49 X |
| 3,475,765 | 11/1969 | Zeltmann | 2/8 |

FOREIGN PATENTS OR APPLICATIONS
565,395  11/1944  United Kingdom...................... 2/8

*Primary Examiner*—Paul A. Sacher
*Attorney, Agent, or Firm*—Elliott I. Pollock

[57] ABSTRACT

Automatically operable protective means, e.g. a helmet, for use by welders, has an eye shading means which is brought automatically into shading condition upon reception of light rays or ultrasonic vibrations by a transducer and electromagnetic operator. Provision is made for supplying cooling air to the electronic and electromagnetic devices and to the eye shade, and the shade may incorporate movable polarizing plates for adjustment of transparency.

1 Claim, 13 Drawing Figures

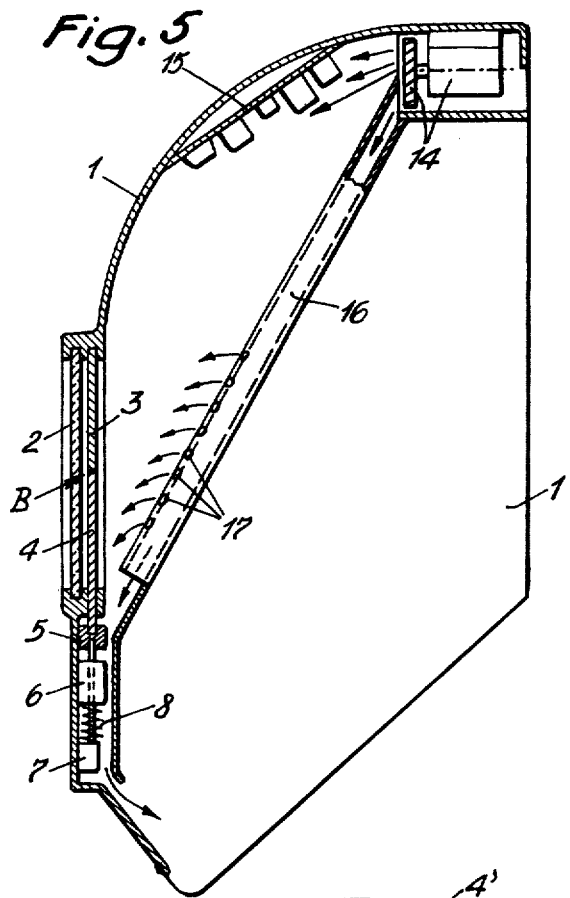
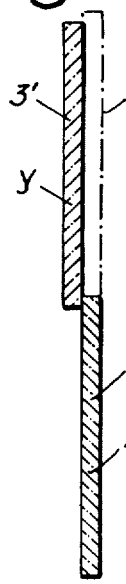
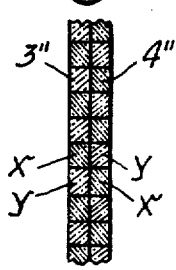
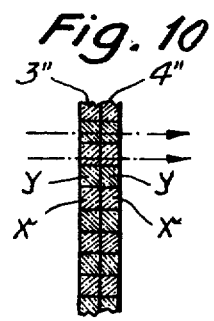
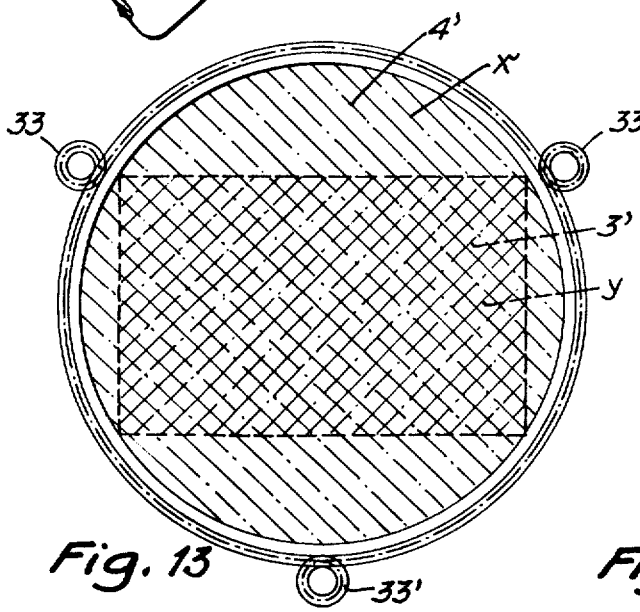
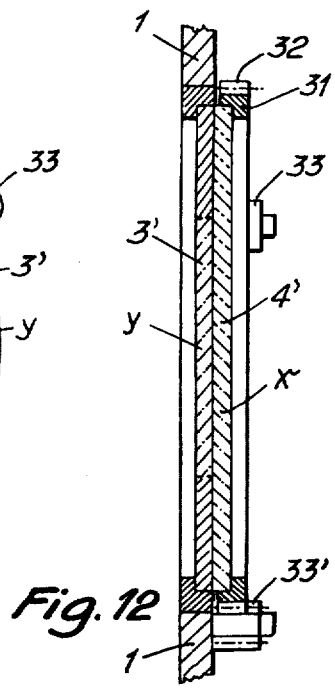

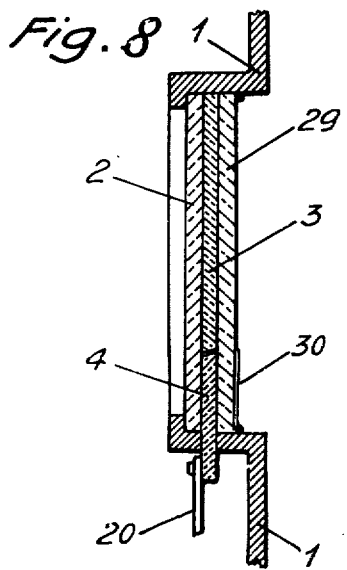
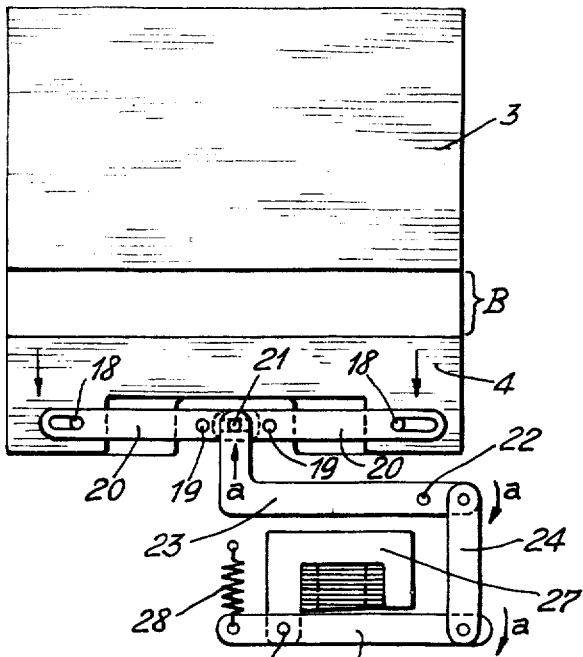
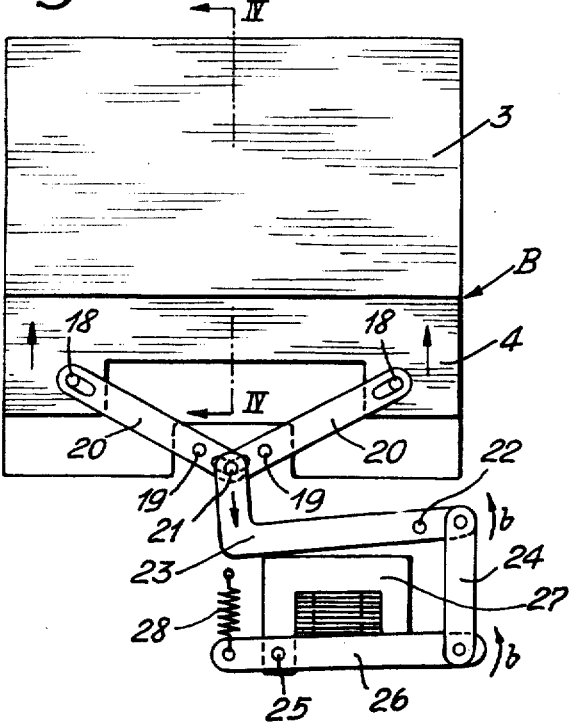

AUTOMATIC PROTECTIVE SHADE EQUIPMENT ON PROTECTIVE VISORS, PROTECTIVE HELMETS OR PROTECTIVE GOGGLES, PARTICULARLY FOR FUSION WELDING

It is known that arc-welding can only be carried out with protective visors or protective helmets because of the occurrence of strong ultraviolet rays from the arc.

Protective visors and protective helmets with vision slits known up to now are equipped with interchangeable dark lenses and thus prevent severe dazzling and penetration by injurious ultraviolet rays. Without the powerful arc, the work to be welded is invisible through the dark protective goggles and so the welder is forced to remove the protective light shield when the electrode is applied. This happens for example by removing the visor, opening the helmet or by a mechanical operation (opening the protective dark goggles).

These operations are carried out manually, thus the welder's eyes are exposed to the injurious rays for a certain time. In many cases this results in eye damage.

When several welders are working in close proximity, the one without the protection of goggles is exposed to the eye-damaging rays of his fellow-workers.

GAS FUSION WELDING

For gas fusion welding (oxy-acetylene welding) goggles with dark lenses are usually worn to protect against the powerful gas flame light, and these frequently have to be pushed up during work.

Since both hands are usually used in oxy-acetylene welding this handling is always a nuisance.

The invention disclosed concerns automatic protective shade equipment on protective visors, protective helmets or protective goggles, in particular for fusion welding, by means of which the disadvantages inherent in previous embodiments are eliminated.

This invention is characterised by the fact that when the arc or the gas flame is lit, the shade is automatically closed in a fraction of a second and thus the penetration of injurious ultraviolet rays and dazzling is completely prevented.

The drawings show examples of embodiments of the subject of the invention as follows:

FIG. 5 is a section through a welding helmet having built-in cooling and ventilation equipment;

FIG. 6 is a view of an attached viewing window when the vision slit is open;

FIG. 7 is a view of the viewing window of FIG. 6 when the vision slit is closed;

FIG. 8 is a part section along the line IV — IV in FIG. 7;

FIG. 9 depicts a second variant of the viewing window;

FIGS. 10 and 11 depict a third variant of the viewing window when the shade is open and closed respectively;

FIG. 12 is a vertical section through a further embodiment of the viewing window, and, FIG. 13 is a plan view of FIG. 12.

Figure 1:
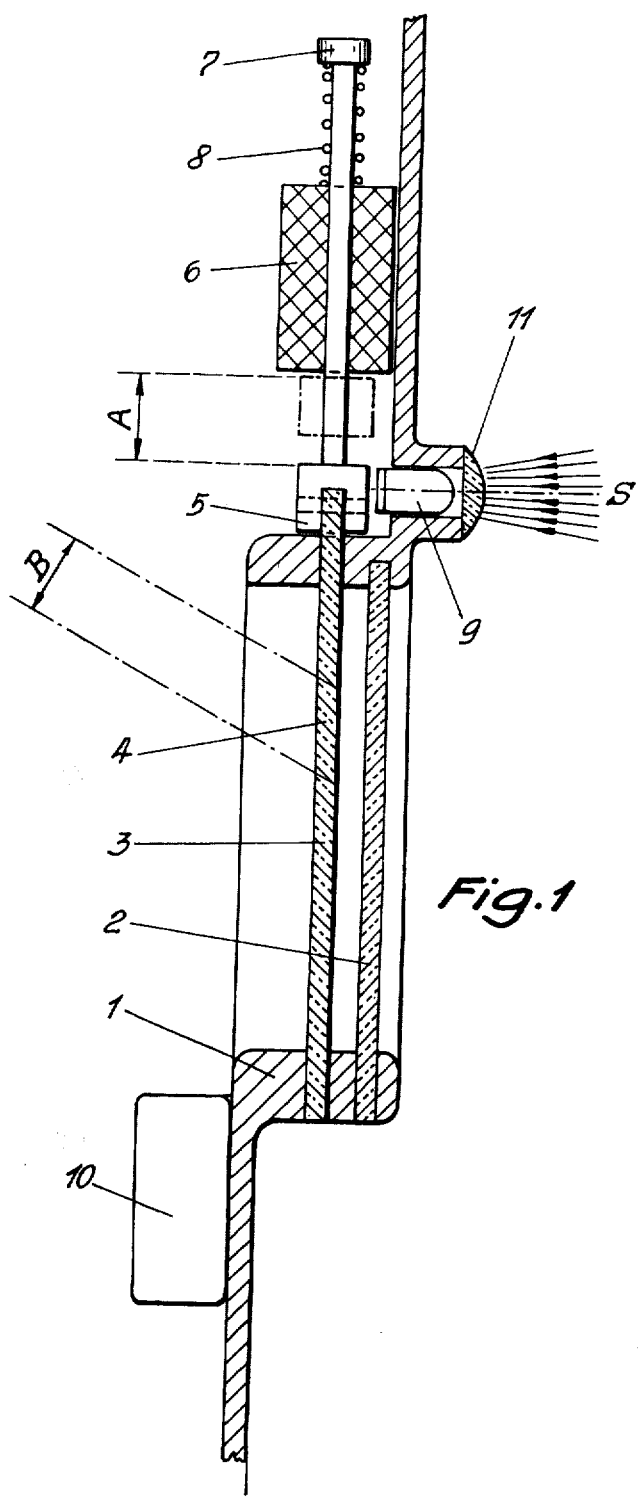
FIG. 1 is a part section through a visor or helmet constructed in accordance with one embodiment of the invention.
Figure 2:
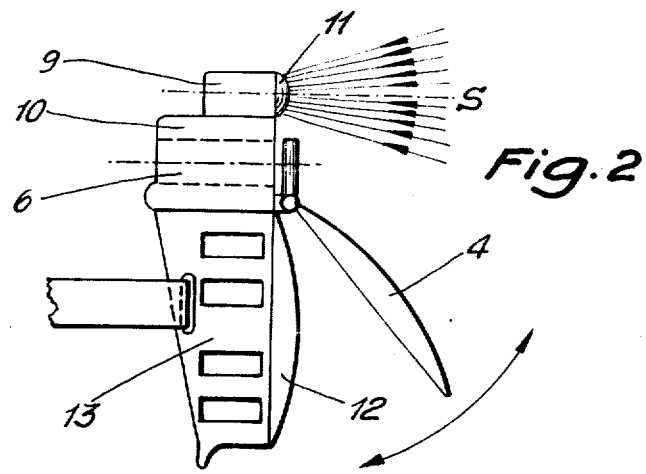
FIG. 2 is a side view of an embodiment of the invention employing goggles with a shade.
Figure 3:
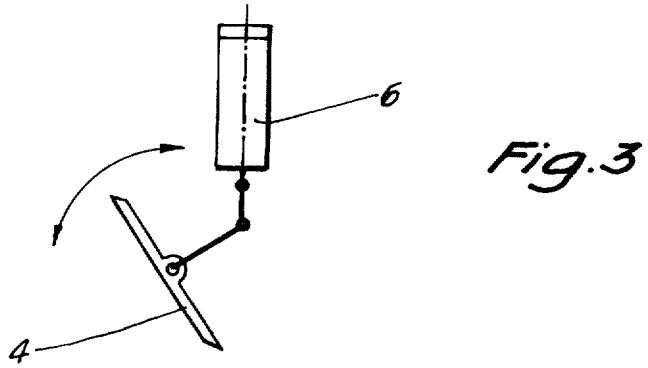
FIG. 3 is a side view of a pivoting flap shade.
Figure 4:
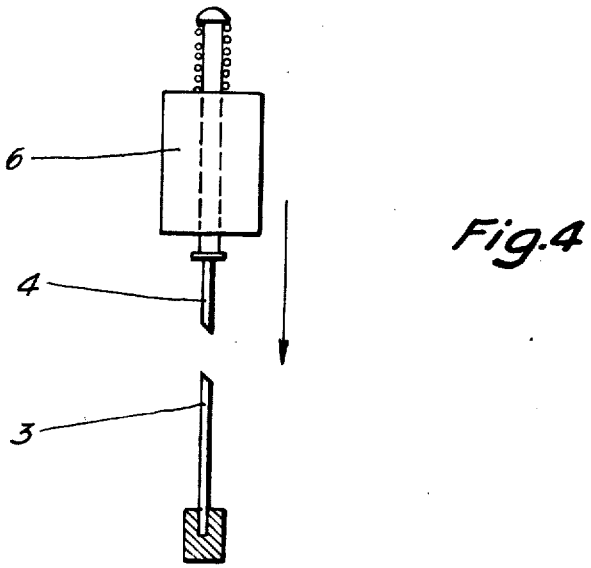
FIG. 4 is a side view of a sliding shade.

In FIGS. 1 and 2, a pulse generator 9 for selectively closing the shade 4 on the shield, respectively, of the helmet 1 or goggles 13, includes an aperture in which a photo-transistor, a photo-diode or photo-resistance or a supersonic receiver is incorporated. The shade 4 may be mounted for translational movement as in FIGS. 1 and 4, or for pivotal movement as in FIGS. 2 and 3. When the light source S is lit, the shade 4 is closed in a fraction of a second by means of the pulse generator 9 which acts supersonically, by means of a control device 10 through an electromechanical magnet or solenoid 6 and 7 the armature 7 of which is arranged to move through a distance A when the coil 6 is energized.

After each interruption of the light source the shade 4 is reopened, after a delay, electro-magnetically by the pulse generator 9 acting via the control device 10 and-/or mechanically by reason of the action of a spring 8 in the solenoid 6, 7 to open (vision aperture B).

The shade 4 is made of known dark glass, plastic with low transparency, or a linear polarizer which prevents the penetration of all eye-damaging rays or reduces the dazzle from the gas flame to a minimum. On most visors or helmets 1 a second ordinary window glass 2 is added to protect the dark glass. If desired, a completely transparent UV-filter can be provided in place of this glass 2.

The aperture B in the shade 4 is large enough for the work in hand to be readily visible through the protective helmet or visor 1 or through the goggles 13.

The pulse generator 9 comprises a transistor, a photo-diode, a photo-eletric cell or a photo-resistance so arranged (in association with a spectrum filter) that it is only actuated to provide an output pulse when the light source S contacts the oxy-acetylene weld.

The photo-electric pulse generator 9 is covered by a tube having a light filter 11 which prevents the activation of the pulse generator by spurious light rays, i.e. light rays which do not lie within the field of vision or in the adjusted spectrum, so that these do not close the shade 4.

When the pulse generator includes a supersonic receiver, the receiver is so tuned that only the controlling supersonic frequency (modulation, welding noise) can activate the pulse.

The control device 10 consists of a transistorized amplifier and comprises ordinary commercial electronic components and is preferably contained in a small plastic housing. The control device 10 is so small that it can readily be incorporated in the visor or helmet 1 adjacent the shade 4 or on the goggles 13 over the lenses 12.

The power necessary to operate the solenoid 6, 7 and the control device 10 is so small that it may preferably be supplied by batteries, which are housed in the helmet itself or may be carried in the user's pocket for reasons of weight; or by rechargeable miniature power sources which are connected by plug and socket to the helmet.

FIG. 5 shows the automatic protective shade equipment incorporated in a protective helmet. Element 2 is the viewing window of the protective helmet in which the protective shade consists of one fixed and one moving part 3 and 4 respectively. In FIG. 5, B indicates the vision aperture in the protective shade. Parts 3 and 4 are made of dark glass. The moving part 4 can in turn be actuated by an electro-magnetic control system 5, 6, 7 and 8. There is a mini-fan 14 incorporated in the upper part of the protective helmet 1, connected to an electronic control system 15. A cold air channel 16 is set laterally in the inner wall of the helmet, which diverts part of the stream of cold air being directed on the electronic assembly and leads directly to the electromagnetic control system 5, 6, 7 and 8. Part of the stream of cold air being conducted through the channel 16 is diverted through apertures 17 made in the side of the channel 16 and ventilates the viewing window thus preventing the latter from misting or steaming-up.

In the embodiment of FIG. 6 the viewing window again has a fixed part 3 and a moving part 4. A pair of levers 20 swivelling around an axle pin 19 engage with two pins 18 on the moving part 4 of the shade. The ends of this pair of levers which abut against each other are connected via an articulating pin 21 to one end of a lever 23 swivelling around an axle pin 22. The other end of the lever 23 is articulated by means of a connecting rod 24 on one end of an anchor rod 26 swivelling around an axle pin 25. The anchor rod 26 is actuated by an electro-magnet 27 against a spring 28. When no current is passing through the electro-magnet 27 the moving part 4 of the shade is pushed down, as shown in FIG. 6, by the system of levers under spring tension in the direction of the arrows *a* into the open position. When the electro-magnet 27 is excited, the anchor rod 26 is pulled against the spring 28 so that the moving part 4 of the shade is pushed upwards, as in FIG. 7, into the closed position, by the pivoting of the system of levers in the direction of the arrows *b*.

In the viewing window in FIG. 8 the outer, completely transparent protective lens is designated as 2. For the shade there is a dark lens 3, 4 in which part 3 is fixed and part 4 movable in a vertical direction and is connected with the lever system of FIG. 7. The inner side of the shade 3, 4 is fitted with a completely transparent UV-filter 29, whose lower section is provided with a thin shiny coating 30 on its inner side in the region of the viewing aperture B, which permits viewing from inside to out, but prevents the passage of injurious rays from outside to in. The filter 29 prevents the passage of ultraviolet rays.

The viewing window illustrated in FIG. 9 comprises a two-part shade 3', 4' whose fixed part 3' acts as a polarizer in the x-axis. The moving shade part 4', which can be actuated by an electro-magnetic control system, is illustrated in the open position and forms a polarizing screen whose polarization is in the y-axis. Since both the polarization panes 3' and 4' run towards each other at an angle of 90° in relation to their axes of polarization, both panes 3' and 4', on their own, i.e. when the shade is open, provide unhindered transparency. When the shade is closed, i.e. when the moving shade 4' is raised to the position indicated by the line of dots and dashes, transparency is reduced to 0.001%, depending on polarization.

In accordance with the variant shown in FIGS. 10 and 11, the panes of the viewing window can be composed of polarizing strips or they can be lined with polarizing strips, so that the strips follow one another polarized alternately in the x- and y-axes, as may be seen in FIGS. 10 and 11. In FIG. 10 the two panes 3'' and 4'' are moved appropriately against each other in such a way that strips having the same polarization are brought into positions covering each other. In this case there is complete transparency. In FIG. 11 the two panes 3'' and 4'' are moved appropriately against each other in such a way that strips having different polarization are brought into positions covering each other. In this case the passage of light is prevented. This method of construction permits a very small sliding movement of the moving shade part 4'' between the open and closed positions, corresponding to the distance X and Y.

FIGS. 12 and 13 show a viewing window with one fixed pane 3' and one pane 4' which can be turned against it through 90°. The movable pane 4' is held in a circular frame which is provided with a toothed system 32 and is mounted in the toothed system so that it may be rotated by three engaging pinions 33, 33'.

The rotational adjustment of the pane 4' in relation to the pane 3' may be made with a gear-rack engaging on pinion 33'. The fixed pane 3', for the sake of example, has a polarization in the y-axis. The moving pane 4' can be so adjusted by rotation that its polarization runs at 90° to that of pane 3', i.e. in the x-axis, as is shown by suitable shading in FIG. 12. This arrangement also enables any desired degree of transparency to be achieved since the moving pane 4' can also be adjusted at any desired angle to the pane between 0° and 90°. When set to 0° both panes 3' and 4' have matching polarization so that there is unhindered transparency, while at 90° the polarization of pane 4' runs along the x-axis.

The direct incorporation of the mini-fan in the helmet does away with the especially troublesome airtubes in welding work which connect the appliance to a stationary fan. In addition, as shown in FIGS. 5–13, the components of the electronic and electro-magnetic control system are protected from overheating by jets of air diverted from the mini-fan.

The invention described permits the use of arc- and oxy-acetylene welding equipment in a way which is more rational and less damaging to the eyes.

I claim:

1. Automatic protective equipment for welders comprising a welding helmet having a transparent outer face plate mounted at a fixed position thereon, a planar protective shade mounted on said helmet closely adjacent to and in generally parallel relation to said face plate at a position between said face plate and the eyes of a wearer of said helmet, said protective shade comprising first and second transparent planar elements mounted for relative linear movement through a predetermined limited distance in a direction parallel to said face plate to selectively define a viewing aperture the width of which is related to said limited distance, an electrically energizable solenoid within said helmet at a position below said protective shade, the armature of said solenoid being connected to one of said planar elements for moving said one planar element in translation in a first direction through said limited distance relative to the other of said planar elements when said solenoid is energized, spring means for urging said one planar element in a second direction opposite to said first direction when said solenoid is de-energized, control means carried by said helmet for controlling the energization of said solenoid, said control means comprising a transducer responsive to incident radiant energy, said transducer being connected to a battery-powered transistorized amplifier the output of which is connected to said solenoid to energize said solenoid when radiant energy produced by a welding operation is incident on said transducer, a motor driven air fan mounted within said helmet adjacent the top of said helmet, air guide means within said helmet for directing a first stream of air from said fan onto said control means, said air guide means including an elongated confined channel extending from the top of said helmet along a side of said helmet past said face plate and protective shade to direct a second stream of air from said fan onto said solenoid, said elongated channel including a plurality of apertures in one wall thereof for diverting a portion of said second stream of air onto said protective shade and face plate, and said air guide means including means defining an air discharge for said first and second streams of air at a position adjacent the bottom of said helmet.

* * * * *